United States Patent [19]

Chang

[11] Patent Number: 4,822,739
[45] Date of Patent: Apr. 18, 1989

[54] PARTITION PROFICIENCY IN GENETICALLY ENGINEERED PLASMIDS FOR TRANSFORMING GRAM-POSITIVE ORGANISMS

[75] Inventor: Shing Chang, Hercules, Calif.

[73] Assignee: Cetus Corporation, Emeryville, Calif.

[21] Appl. No.: 814,179

[22] Filed: Dec. 24, 1985

Related U.S. Application Data

[63] Continuation of Ser. No. 470,576, Feb. 28, 1983, abandoned, which is a continuation-in-part of Ser. No. 384,253, Jun. 2, 1982, abandoned.

[51] Int. Cl.[4] .................... C12N 15/00; C12N 1/20; C12N 1/00; C07H 15/12
[52] U.S. Cl. ............................... 435/172.3; 435/320; 435/252.31; 536/27
[58] Field of Search .................... 435/172.3, 253, 317, 435/320; 536/27

[56] References Cited

FOREIGN PATENT DOCUMENTS 2048894 12/1980 United Kingdom .

OTHER PUBLICATIONS

Tanaka et al, J. Bacteriology, vol. 129, No. 3, pp. 1487–1494 Mar. 1977.
Meacock et al, Cell, vol. 20, pp. 529–542 Jun. 1980.
Eholich, PNAS, vol. 75, pp. 1433–1436, Mar. 1978.
Gryczan et al, Mol. Gen. Genet, vol. 177, pp. 459–467 (1980). .

*Primary Examiner*—Alvin E. Tanenholtz
*Attorney, Agent, or Firm*—Virginia H. Meyer; Jane R. McLaughlin; Albert P. Halluin

[57] ABSTRACT

Methods and compositions are described which can be used to enhance the stability of genetically engineered plasmids in Gram-positive organisms. Also described are genetically engineered plasmids comprising a DNA fragment which enhances their stability and Gram-positive organisms transformed with such plasmids.

8 Claims, 4 Drawing Sheets

PARTITION PROFICIENCY IN GENETICALLY ENGINEERED PLASMIDS FOR TRANSFORMING GRAM-POSITIVE ORGANISMS

This application is a continuation application of application Ser. No. 470, 576, filed Feb. 28, 1983, abandoned, which is in turn a continuation-in-part of application Ser. No. 384,253, filed Jun. 2, 1982, abandoned.

This invention relates generally to the field of molecular biology and specifically to a method for conferring long term stability to engineered recombinant plasmids which propagate in Gram-positive organisms.

The method of the invention is used to construct novel engineered recombinant plasmids that are stably propagated within a growing population of Gram-positive organisms. A parental plasmid that can be used to construct the novel engineered recombinant plasmids of the invention is pLS11. Plasmid pLS11 is found in *Bacillus subtilis* strain IFO3022 which is on deposit at the Institute for Fermentation in Osaka, Japan. Strain IFO3022 is available without restriction to anyone who requests it. An example of a novel plasmid constructed according to the method of the present invention in *Bacillus subtilis* strain BD224 has been deposited in the American Type Culture Collection, Rockville, Md., 20852. This plasmid is identifed as plasmid pOG2381. *Bacillus subtilis* strain BD224 harboring pOG2381 has been assigned ATCC Number 39038. Applicant has directed that the strain and plasmid be freely available to the general public upon the issuance of a United States patent.

In order for autonomously replicating plasmids to be propagated stably within a growing bacterial cell population, several requirements must be satisfied. The rate of plasmid replication must be monitored by some cellular mechanism and adjusted to the growth rate of the culture. It has been suggested that this is probably accomplished through the action of a cytoplasmic agent which acts to regulate the frequency of replication initiation of the plasmid DNA molecule. The alleged cytoplasmic agent appears to be synthesized in proportion to the number of plasmid copies. See Pritchard, R., et al., *Symp. Soc. Gen. Microbiol.*, 19:263-297 (1968). In this way the plasmid is maintained at a constant concentration within the total cellular mass.

Stable maintenance of a plasmid in a growing cell population also requires that each of the daughter cells produced during cell division receive at least one copy of the plasmid from the parental cell. However, without a mechanism for the active partitioning of the plasmid, distribution of the plasmid molecules between the daughter cells would occur purely by random and a finite proportion of the cells would not inherit the plasmids. Since loss of naturally occurring plasmids is ordinarily not observed during growth of bacterial cell populations, it is now believed that most such plasmids undergo active partitioning at the time of cell division. See Meacock, P. and Cohen, S., *Cell* 20:529-542 (1980).

Stable maintenance of a plasmid in a growing cell population further requires structural stability of the plasmid DNA. When used in this manner, structural stability means faithful propagation of the plasmid DNA during replication.

The present invention relates to the component of stable plasmid propagation which involves active partitioning, i.e. partition proficiency. The invention is significant because, unfortunately, the "engineered" plasmids constructed by modern recombinant DNA techniques do not always undergo active partitioning at the time of host cell division. That is, many engineered recombinant plasmids are not partition proficient or are only weakly so. Lack of active partitioning is especially evident when genetic fragments taken from plasmids native to one type of organism are used in the construction of engineered recombinant plasmids capable of transforming another type of organism. For example, genetic fragments from plasmids native to *Staphylococcus aureus* bacteria have been used in the construction of synthetic plasmids capable of transforming *Bacillus subtilis* bacteria. Construction of such plasmids is described in European Patent Application Publication Number 0,036,259 published Sept. 23, 1981 in Bulletin 81/38. That application has been assigned to the assignee of the present application.

Recent research directed to industrial applications of plasmids of the type described in European Patent Application Publication Number 0,036,259 demonstrated that such engineered recombinant plasmids and their progeny are not always stably maintained during cell population growth because they are not actively partitioned in cell divisions. Of course, lack of stable maintenance during cell population growth diminishes the industrial usefulness of engineered recombinant plasmids constructed to code for useful gene products. The maintenance of such structurally stable but not actively partitioned plasmids requires the presence in the growth medium of an antibiotic, or another type of selection pressure, against which the plasmid provides a selective advantage to cells harboring it. Stably maintaining plasmids in this way, e.g., with an antibiotic in the growth medium, is costly and inefficient.

It is an object of the present invention to provide a method for producing engineered recombinant plasmids capable of transforming Gram-positive organisms that will be actively partitioned during host cell division and stably maintained during host cell population growth.

Another object of the invention is to provide a method for producing engineered recombinant plasmids capable of transforming *Bacillus subtilis* bacteria that will be actively partitioned during cell division and stably maintained during host cell population growth.

Another object of the invention is to provide engineered recombinant plasmids capable of transforming Gram-positive organisms that will be actively partitioned during host cell division and stably transmitted during host cell population growth.

Another object of the invention is to provide engineered recombinant plasmids capable of transforming *Bacillus subtilis* bacteria that will be actively partitioned during host cell division and stably maintained during host cell population growth.

Another object of the invention is to provide DNA fragments comprising a partition proficiency gene which, when incorporated into engineered recombinant plasmids capable of transforming Gram-positive organisms, render the "Gram-positive" engineered recombinant plasmids partition proficient during host cell division.

Another object of the invention is to provide DNA fragments comprising a partition proficiency gene which, when incorporated into plasmids capable of transforming *Bacillus subtilis* host organisms, render the *Bacillus subtilis* engineered recombinant plasmids partition proficient during host cell division.

Another object of the invention is to provide Gram-positive host organisms transformed by engineered recombinant plasmids that are partition proficient during the organisms' cell division.

Another object of the invention is to provide *Bacillus subtilis* host organisms transformed by engineered recombinant plasmids that are partition proficient during the *Bacillus subtilis* organisms' cell division.

A still further object of the invention is to provide a method for obtaining a DNA fragment which comprises a partition proficiency gene for plasmids capable of transforming Gram-positive organisms.

Other objects of the invention will become apparent to those skilled in the art from the following description, taken in connection with the accompanying drawing wherein:

Very generally, the invention discloses a method useful in the production of engineered recombinant plasmids that will be partition proficient and stably transmitted during Gram-positive host cell divisions and stably maintained during growth of host cell populations. Engineered recombinant plasmids produced by the method of the invention are capable of replication in Gram-positive organisms and include a partition segment, par+, which confers the partition proficiency in host cell divisions and is required for stable maintenance of the engineered recombinant plasmids within growing Gram-positive host cell populations. The engineered recombinant plasmids can include DNA coding for a desired protein or other gene products.

As used herein, engineered recombinant plasmid means a plasmid constructed using techniques of genetic engineering.

Techniques of genetic engineering mean techniques which lead to the formation of new combinations of heritable material by the insertion of nucleic acid molecules, produced or derived by whatever means outside the cell, into a bacterial plasmid or other vector system so as to allow their incorporaton into a host organism in which they do not naturally occur at high frequency but in which they are capable of replication.

A Gram-positive organism means a Gram-positive bacterium.

A transformable host means a Gram-positive host organism capable of accepting plasmid DNA from Gram-positive par+ recombinant plasmids. Gram-positive transformable host organisms are thus capable of being transformed by Gram-positive par+ recombinant plasmids.

A compatible host organism means a transformable Gram-positive host organism capable of allowing replication of the par+ recombinant plasmid DNA. Said compatible host organism will also allow expression of the par+ phenotype, in addition to at least one other gene carried the Gram-positive par+ recombinant plasmids.

Progeny means offspring or daughter cells produced during cell division where the offspring or daughter cells are substantially equivalent to the parental cell.

Partitioning means the process, random or active, whereby copies of a plasmid are distributed or transmitted to daughter cells during host cell division.

Active partitioning means partitioning of plasmids in a partition proficient plasmid-host cell system.

Partition proficiency is a phenotypical trait of a plasmid in a cell such that copies of the plasmid are partitioned in cell division by other than purely random processes. Partition proficiency in a plasmid-Gram-positive host cell system requires the presence of a Gram-positive partition segment on the plasmids of such a system.

The Gram-positive partition segment comprises a sequence of DNA nucleotides, herein defined as a partition proficiency gene (par+), which must be on a plasmid for partition proficiency.

If a plasmid lacks the partition proficiency gene, the plasmid will be unevenly partitioned during cell division. Unless the plasmid confers a selective advantage on cells harboring it, its prevalence in the host cells may decrease at a substantial rate after several generations of cell divisions. Thus production of useful gene products from genes carried on the plasmids may diminish or stop entirely.

The par+ segment can be derived from naturally occuring Gram-positive plasmids. Examples of such plasmids have been described by Tanaka, T., et al., *J. Bacteriol.*, 129:1487–1494 (1977). The par+ segment can also be obtained from engineered recombinant plasmid pOG2381 (ATCC 39038).

An engineered recombinant par+ plasmid of the invention will have a stability in growing, Gram-positive host cell populations that is greater than that of an engineered recombinant plasmid that is structurally the same but for lack of the partition segment. Par+ engineered recombinant plasmids of this invention may be obtained having stability as high as 100% after at least 100 generations of Gram-positive host cell growth. As used herein, one generation means a doubling of host cell number.

In practicing the method of the invention, naturally occurring Gram-positive plasmids that contain the par+ function are cleaved with restriction enzymes to create linear DNA segments having ligatible termini. The partition proficiency gene will be contained on some of the linear DNA fragment segments (Gram-positive partition segments). The partition proficiency gene can also be obtained from engineered recombinant plasmid pOG2381 (ATCC 39038). Plasmid pOG2381 is cleaved with restriction enzymes to yield a fragment which contains the partition proficient gene. Cleavage with restriction enzymes MboI or Sau3A yields a large fragment of about 1200 bp (1.2 kb) which includes the partition proficient gene. Cleavage with restriction enzymes HaeIII and HindIII yields a smaller fragment of about 350 base pairs which also includes the partition proficient gene. Cleavage of pOG2381 with restriction enzymes PstI and HaeIII yields a still smaller fragment of about 260 bp which includes the partition proficient gene. Recombinant plasmids capable of replication in Gram-positive host organisms are also cleaved with restriction enzymes to yield linear DNA having termini ligatable with the termini of Gram-positive partition gene segments. The termini are bound together to form novel recombinant plasmids used to transform transformable and compatible Gram-positive host organisms. After transformation, the cells are grown and selection is made for partition proficient (par+) plasmids. Transformants carrying the par+ plasmids are harvested and used in applications where long term growth or fermentation for the production of protein or other gene products is desired.

In a preferred form of the present invention the partition proficient gene is derived from the naturally occurring *Bacillus subtilis* plasmid pLS11 from strain IFO3022, described by Tanaka T., et al., *J. Bacteriol.*, 129:1487-1494 (1977). Strain IFO3022 is on deposit at the Institute for Fermentation in Osaka, Japan. It is available without restriction to anyone who requests it. Plasmid pLS11 is isolated and purified from *Bacillus subtilis* strain IFO3022 using methods described by Tanaka et al, supra. Following its isolation and purification, plasmid pLS11 is digested with the restriction enzyme MboI (New England Biolabs, Inc. Beverly, Me. 01915) using techniques known to the art. Enzyme conditions are those recommended by the manufacturer. Enzyme digestion of pLS11 generates about 10 DNA fragments. The partition proficient gene is contained on an MboI fragment of about 1.2 kb. Also preferred as a source of the partition proficiency gene are the 260 bp HaeIII - PstI fragment, the 350 bp HaeIII - HindIII fragment, or 1.2 kb MboI or Sau3A fragment from plasmid pOG2381 (ATCC 39038). These Gram-positive partition segments (also described herein as Gram-positive par+ fragments) are then ligated into a compatible restriction enzyme site on an engineered recombinant plasmid capable of transforming Gram-positive bacteria. Especially preferred as engineered recombinant plasmids are the recombinant plasmids disclosed in European Patent Application Publication Number 0,036,259. The novel engineered recombinant plasmids carrying the Gram-positive par+ fragment are used to transform transformable and compatible Gram-positive host cells. Especially preferred is *Bacillus subtilis* strain BD224 (trpC2 thr-5 recE4). Transformants are selected and then inoculated into broth without antibiotics and grown for about 50 generations to allow the unstable partition deficient, par−, clones to segregate. Transformants carrying the par+ plasmids are harvested and used in the production of desired gene products.

The following examples illustrate ways in which the invention may be employed. They are included only for purposes of illustration and are not intended to limit the scope of the invention in any way.

EXAMPLE 1

Construction of engineered recombinant plasmids containing a Gram-positive partition fragment, par+, from a *Bacillus subtilis* plasmid.

Plasmid pLS11 was isolated and purified from *Bacillus subtilis* strain IFO3022. See Tanaka, T., et al., *J. Bacteriol.*, 129:1487-1494, (1977). Two micrograms of pLS11 DNA were digested with 2 units of restriction enzyme MboI, (New England Biolabs, supra), in 50 microliters of 6 mM Tris-HCl, pH 7.5, 6 mM $MgCl_2$, 50 mM NaCl, at 37° C. for 30 minutes.

Plasmid DNA from pLS11 was ligated with DNA originating from the engineered recombinant plasmids described in European Patent Application Publication Number 0,036,259. Specifically, DNA from pLS11 was ligated with DNA from plasmid pOG2326.

Figure 1:
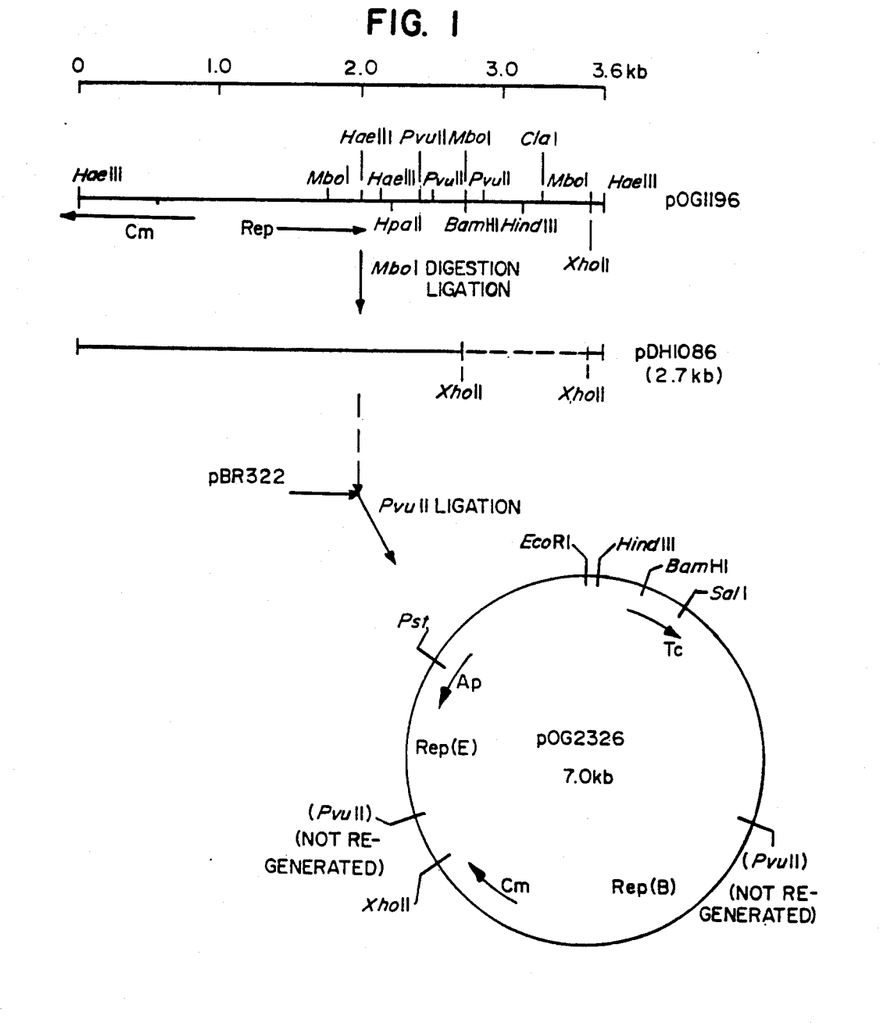
FIG. 1 shows restriction enzyme maps that detail the construction of plasmid pOG2326.
Figure 3:
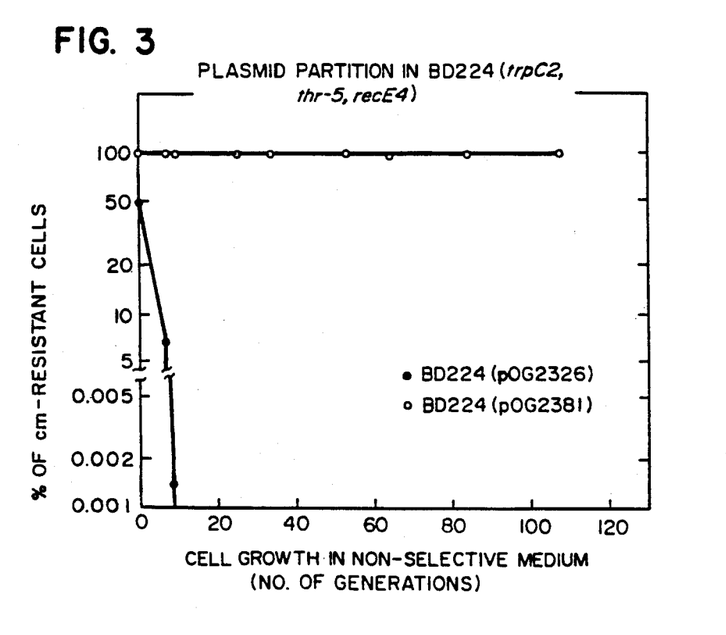
FIG. 3 is a graph that illustrates partition proficiency of plasmid pOG2381 which is stably maintained, and pOG2326 which is not stably maintained, in populations of *Bacillus subtilis* strain BD224 growing in the absence of the antibiotic chloramphenicol. The stable maintenance of pOG2381 demonstrates its partition proficiency. The lack of stable maintenance of pOG2326 is due to its lack of partition proficiency.

Plasmid pOG2326, which replicates in both *Bacillus subtilis* and *Escherichia coli* was constructed from *Bacillus subtilis* plasmid pOG1196 (ATCC 31776) and *Escherichia coli* plasmid pBR322 (ATCC 37017). See FIG. 1. In constructing pOG2326, 3 micrograms of DNA from plasmid pOG1196 was digested with MboI enzyme under the same conditions described above for pLS11 DNA. The digested DNA was ligated with 2 units of T4-DNA ligase in 20 microliters of 66 mM Tris-HCl, pH 7.6, 6.6 mM $MgCl_2$, 10 mM DTT, 0.1 mM ATP, at 14° C. for 18 hours. After transformation of *Bacillus subtilis* BD224 with the ligated DNA, a plasmid-carrying, chloramphenicol-resistant transformant was characterized further. The plasmid found in the transformant was designated pDH1086; it had the same structure as pOG1196 except that a small MboI fragment has been deleted. See FIG. 1. Two micrograms each of plasmid pHD1086 and *Escherichia coli* plasmid pBR322, were digested with PvuII endonuclease under the same conditions described above for MboI. The resulting fragments were ligated with T4-DNA ligase using procedures described supra for this ligase. The ligated DNA was used to transform *Escherichia coli* strain CS412 (an hsdR− derivative of C600 strain); transformants resistant to chloramphenicol were selected. The plasmid from one transformant, designated pOG2326, was characterized further. It has the structure shown in FIG. 1. The low stability of plasmid pOG2326 was shown by the fact that, after 10 generations in broth without antibiotics, less than 0.002% of the cells in a population still harbored the plasmid, when assayed using chloramphenicol (Cm) resistance as described below. These data are shown in FIG. 3.

In constructing plasmid pOG2381, 0.5 micrograms of DNA from plasmid pOG2326 was digested with BamHI enzyme; then 2 micrograms of the MboI fragments of pLS11 were added. The pOG2326 fragments and the pLS11 fragments were ligated with T4-DNA ligase using procedures described supra for this ligase. The ligated DNA was used to transform *Escherichia coli* strain CS412 (an hsdR− derivative of C600 strain). Those skilled in the art will recognize that any other hsdR− strain of *Escherichia coli* could have been used in this transformation.

Since insertion into the BamHI site inactivates the tetracycline resistant (tet) gene, *Escherichia coli* transformants harboring chimeric plasmids containing cloned pLS11 sequences showed ampicillin - resistant, tetracycline - sensitive ($Ap^R Tc^S$) phenotype. One hundred $Ap^R$ transformants were tested; 47% of $Ap^R$ clones carried recombinant plasmids derived from pOG2326. Plasmid DNA was made from a mixed culture of about one hundred ampicillin-resistant, tetracycline-sensitive ($Ap^R Tc^S$) transformants. The plasmid DNA was then transformed into *Bacillus subtilis* strain BD224 (trpC2 thr-5 recE4). Transformants were selected initially on Cm-containing plates. Following this selection, about one thousand of the selected clones were innoculated into broth without antibiotics and grown for about 50 generations. This allowed unstable partition deficient, par−, clones to segregate. This culture was then grown overnight in Cm-containing broth to enrich for the par+ clones. After two more cycles of this type of segregation-enrichment treatment, eight individual clones were isolated to test for par+ phenotype. They were all 100% stable. Stability was tested by growing transformed BD224 strain in broth without antibiotics for 100 generations. One hundred or more colonies from each culture were grown up on plate and tested individually for resistance to Cm. One plasmid, pOG2381, ATCC Number 39038, isolated from these clones was characterized further. It contains an MboI insert of about 1.2 kb at the BamHl site of pOG2326. Upon transformation into BD224, it again showed par+ phenotype demonstrating that the phenotype is associated with sequences on the plasmid.

To further verify that the par+ fragment is located within a 1.2 kb MboI fragment from pOG2381, the plasmid was digested with Sau3A. Both Sau3A and MboI recognize the same DNA sequences:

5'...GATC...3'
3'...CTAG...5'.

After purification, the 1.2 kb Sau3A fragment was cloned into the BamHl site of pOG2326. The resulting construction was par+ and showed a structure identical to pOG2381. This demonstrates that the partition proficient gene is located within a MboI or Sau3A 1.2 kb fragment from pOG2381. This fragment carries the Gram-positive partition segment.

EXAMPLE 2

Demonstration that *Bacillus subtilis* par+ does not function in *Escherichia coli*.

It has been documented that a partition function is required for stable maintenance of *Escherichia coli* plasmids in *Escherichia coli*. See Meacock, P., and Cohen, S., *Cell*, 20:529–542 (1980). Since some cloned *Bacillus subtilis* genes are functional in *Escherichia coli*, the cloned *Bacillus subtilis* par+ plasmids were tested in *Escherichia coli* strain CS412 using methods described in Example 1. When tested for partition, both plasmids pOG2326 and pOG2381 were phenotypically par− in *Escherichia coli*. After one hundred generations, grown in broth without antibotics, no Ap$^R$ clone was detected among the one hundred clones tested.

EXAMPLE 3

Construction of engineered recombinant plasmids containing a Gram-positive partition fragment, par+, from a *Bacillus subtilis* plasmid, and a heterologous gene coding for a secreted protein product.

Figure 4:
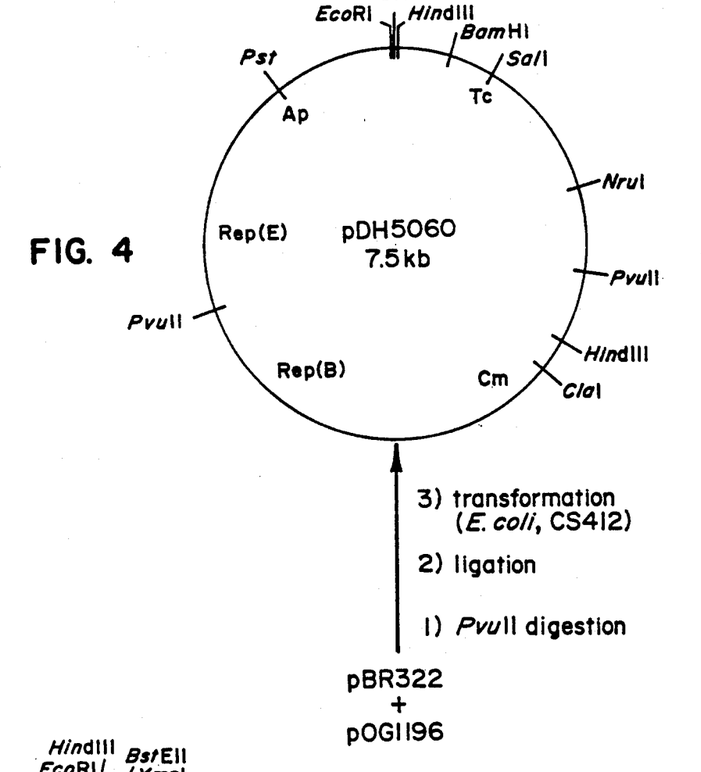
FIG. 4 shows a restriction enzyme map that details the construction of plasmid pDH5060.

To ascertain whether the presence of the Gram-positive partition fragment interferes with the expression and secretion of protein product in Gram-positive bacteria, a plasmid was constructed that carries both the Gram-positive par+ fragment and a heterologous gene coding for a protein known to be expressed and secreted in *Bacillus subtilis*. The plasmid thus constructed has been designated pOG2428. In constructing plasmid pOG2428, a hybrid plasmid was made first that carried sequences from *Escherichia coli* plasmid pBR322 (ATCC 37017) and *Bacillus subtilis* plasmid pOG1196 (ATCC 31776). *Escherichia coli* plasmid pBR322 has been described by Sutcliffe, J. G., *Nucleic Acids Res.* 5:2721–2728 (1978), and *Cold Spring Harbor Symp. Quant. Biol.* 43:77–90 (1979). *Bacillus subtilis* plasmid pOG1196 has been described by Gray, O., and Chang, S., *J. Bacteriol.* 145:422–428 (1981). Plasmids pBR322 and pOG1196 where each digested with the PvuII restriction enzyme and then ligated and transformed into CS412 strain of *Escherichia coli*; chloramphenicol resistant transformants were selected. A plasmid from one transformant, plasmid pDH5060 was utilized futher. A restriction enzyme map of pDH5060 is shown in FIG. 4. The conditions used for digestion and ligaton of the plasmid fractions, as well as transformation of the host, and selection are standard procedures well known to those skilled in the art of recombinant DNA. These and other molecular cloning techniques utilized in practicing the present invention can be found in Maniatis, T., et al., *Molecular Cloning: A Laboratory Manual*, Cold Spring Harbor Laboratory (1982).

Plasmid pDH5060 was digested with restriction enzymes EcoRI and BamHI. The "large plasmid fragment" produced by this enzyme digestion was purified from an agarose gel as described by Maniatis, T., et al, supra.

To provide a gene coding for a heterologous protein known to be expressed and secreted in *Bacillus subtilis*, an EcoRI-BamIII-enzyme generated fragment containing the *Bacillus licheniformis penP* gene was purified from plasmid pSYC310-2. This plasmid has been described by McLaughlin, J., et al., *Nucleic Acid Res.* 10:3905–3919 (1982). Those skilled in the art will realize the *Bacillus licheniformis penP* could have been obtained from other sources. See Gray, O., and Chang, S., *J. Bacteriol.* 145:422–428 (1981). The purified "large fragment" from plasmid pDH5060 and the fragment containing the *Bacillus licheniformis penP* gene from plasmid pSYC310-2 where ligated and transformed into *Escherichia coli* strain CS412; transformants resistant to ampicillin were selected. A plasmid from one transformant, designated pSYC189 was utilized further.

In the plasmid, pSYC189, a small deletion was made in the bla gene which originated from retained portion of the plasmid pBR322. See Sutcliffe, J. G., *Cold Spring Harbor Symp. Quant. Biol.* 43:77–90 (1979). The bla gene encodes beta-lactamase protein. To generate the small deletion in the beta-lactamase gene, the plasmid was digested at the PvuI site in the bla gene. The resulting PvuI digested plasmid DNA was treated with exonuclease BAL-31 using conditions well-known to those skilled in the art. Such conditions are described in Maniatis, T., et al., supra. The BAL-31 treated fragment was recircularized by ligation. This digestion deleted about 120 base pairs from the wild-type sequence of beta-lactamase gene, resulting in a plasmid designa pSYC274.

At the 3'-end of the penicillinase gene in plasmid pSYC274 there is a restriction site for BclI comprising of the recognition sequence: TGATCA. The location of this restriction enzyme site can be found in the sequence reported by Neugebauer, K., et al., *Nucleic Acids Research* 9:2577–2588 (1981). The BclI site is at the nontranslated region near the very end of the penicillinase gene. The BclI site at the end of penicillinase gene is a unique site for this enzyme on plasmid pSYC274.

Digestion with BclI leaves GATC protruding ends which may be ligated with GATC protruding ends generated when DNA is digested with MboI. The 1.2 kb partition fragment from pOG2381 was excised by digesting the plasmid with MboI. The 1.2 kb MboI partition fragment thus obtained was cloned into the BclI site of pSYC274. Ligation of these two plasmid fragments generated a hybrid plasmid designated pOG2428. This plasmid contains the penicillinase gene from *Bacillus licheniformis*, which codes for a product secreted by *Bacillus subtilis* transformed hosts; the plasmid also contains the Gram-positive partition fragment.

EXAMPLE 4

Demonstration that the presence of a Gram-positive par+ fragment does not interfere with the expression or secretion or a heterologous protein produced by transformed *Bacillus subtilis* bacteria.

Gray and Chang have shown that the cloned beta-lactamase, hereinafter referred to as penicillinase or penP, gene from *Bacillus licheniformis* is functionally expressed in *Bacillus subtilis*. See Gray, O. and Chang, S., *J. Bacteriol.* 145:422–428 (1981). The heterologous penicillinase molecules produced in transformed *Bacillus subtilis* cells are translocated across the limiting membrane and subsequently processed proteolytically to form the penicillinase exoenzyme.

To determine whether the presence of the Gram-positive par+ interferred with the expression or secretion of *Bacillus licheniformis* penicillinase by transformed *Bacillus subtilis* host organisms, plasmid pOG2428 was transformed into *Bacillus subtilis* strain BD224. When penicillinase activity in solution was determined spectrophotometrically using nitrocefin (chromogenic cephalosporin 87/312, available from Glaxo Research Limited) by the method of O'Callaghan, C., et al., results showed that there where no decrease in detectable enzyme activity due to the presence of the par+ fragment on pOG2428. See O'Callaghan C., et al., *Antimicrob. Agents Chemother* 1:283–288 (1972).

EXAMPLE 5

The Gram-positive partition function is located within a fragment of about 350 base pairs contained within the larger 1.2 kb MboI fragment.

Figure 2:
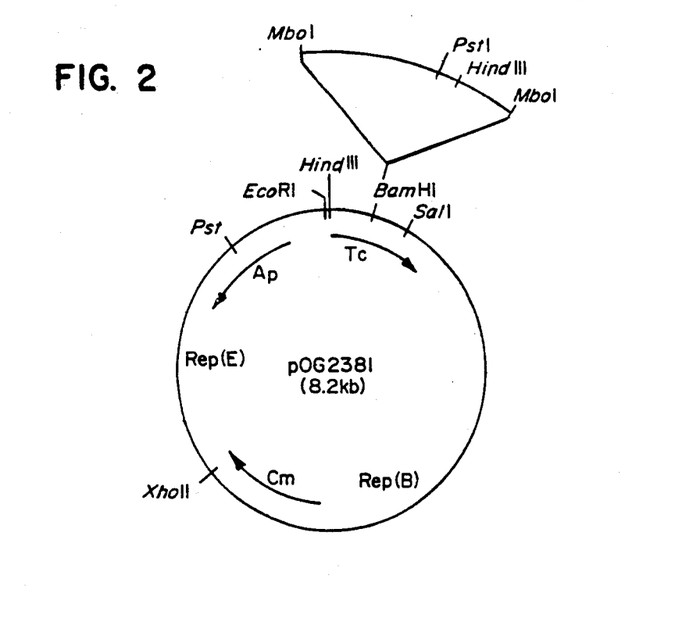
FIG. 2 shows a restriction enzyme map that details construction of plasmid pOG2381 (ATCC 39038).

The 1.2 kb MboI fragment contains a HindIII restriction site. See FIG. 2. Mapping with restriction enzymes revealed a HaeIII site located about 350 base pairs away from the HindIII in the 1.2 kb MboI fragment. Double digestion of plasmid pOG2381 with restriction enzymes HaeIII and HindIII made it possible to purify this 350 base pair fragment from an agarose gel. The purified 350 base pair fragment was cloned into an engineered recombinant plasmid to determine whether the Gram-positive partition function was located within this smaller 350 bp fragment.

Plasmid pDH5060 was treated with HindIII enzyme so that it would only partially cut at one of the two HindIII sites located on that plasmid. The locations of the HindIII sites in plasmid pDH5060 are illustrated in FIG. 4. The partially digested pDH5060 DNA preparation was treated with *Escherichia coli* DNA polymerase I Klenow fragment as described by Maniatis, T., et al., supra. After the HindIII generated protruding ends had been filled in with the *Escherichia coli* DNA polymerase I Klenow fragment, they where ligated using standard methods. The ligated DNA was transformed into *Escherichia coli* strain CS412 competent cells. The transformed *Escherichia coli* cells were screened and a clone was identified which carried a plasmid that had lost one of the two HindIII sites. This plasmid is designated pLP1201. It retains the HindIII site located in the tetracycline gene but has lost the HindIII site that originated from the bacillus replicon.

Figure 5:
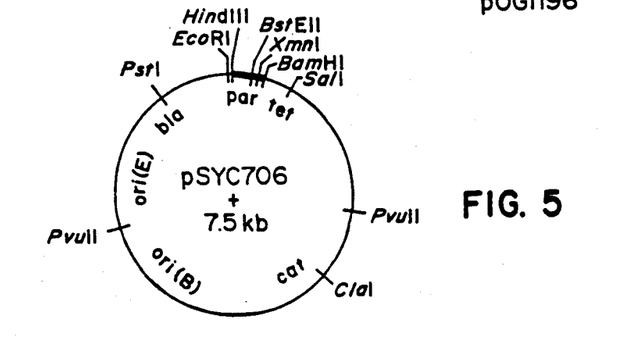
FIG. 5 shows a restriction enzyme map of plasmid pSYC706.

Plasmid pLP1201 was digested with HindIII and BamHI restriction enzymes. BamHI was used first. Once the BamHI protruding ends had been filled in with *Escherichia coli* DNA polymerase I Klenow fragment, the plasmid was digested with HindIII. A partition fragment of approximately 350 base pairs obtained by the method described above was added to this DNA preparation. The DNA mixture was ligated, and then used to transform *Escherichia coli* strain CS412 competent cells. The transformants were screened by isolating and analyzing the DNA structures for the presece of the partition fragment. When a repaired BamHI site is ligated to a HaeIII site, a BamHI site will be regenerated. Thus it was possible to first simply digest plasmid DNA prepared from the transformants, and then identify the desirable transformant which had the HindIII to BamHI fragment of appropriate size. A transformant carrying a plasmid designated pSYC706 was deemed to have the HindIII to BamHI fragment of appropriate size. The structure of pSYC706 is shown in FIG. 5. When *Bacillus subtilis* strain 224 carrying plasmid pSYC706 was tested for partition proficiency, it was shown to have a phenotype identical to plasmid pOG2381. *Bacillus subtilis* cells BD224 harboring plasmid pSYC706 did not spontaneously lose the plasmid as did *Bacillus subtilis* cells BD224 carrying the parental plasmid. This experiment clearly demonstrated that the approximate 350 base pair sequence located between the HindIII site and the HaeIII site in the 1.2 kb MboI fragment contains the Gram-positive partition proficiency function.

EXAMPLE 6

The Gram-positive partition function is located within a fragment of about 260 base pairs contained within the 350 bp HindIII - HaeIII fragment.

Figure 6:
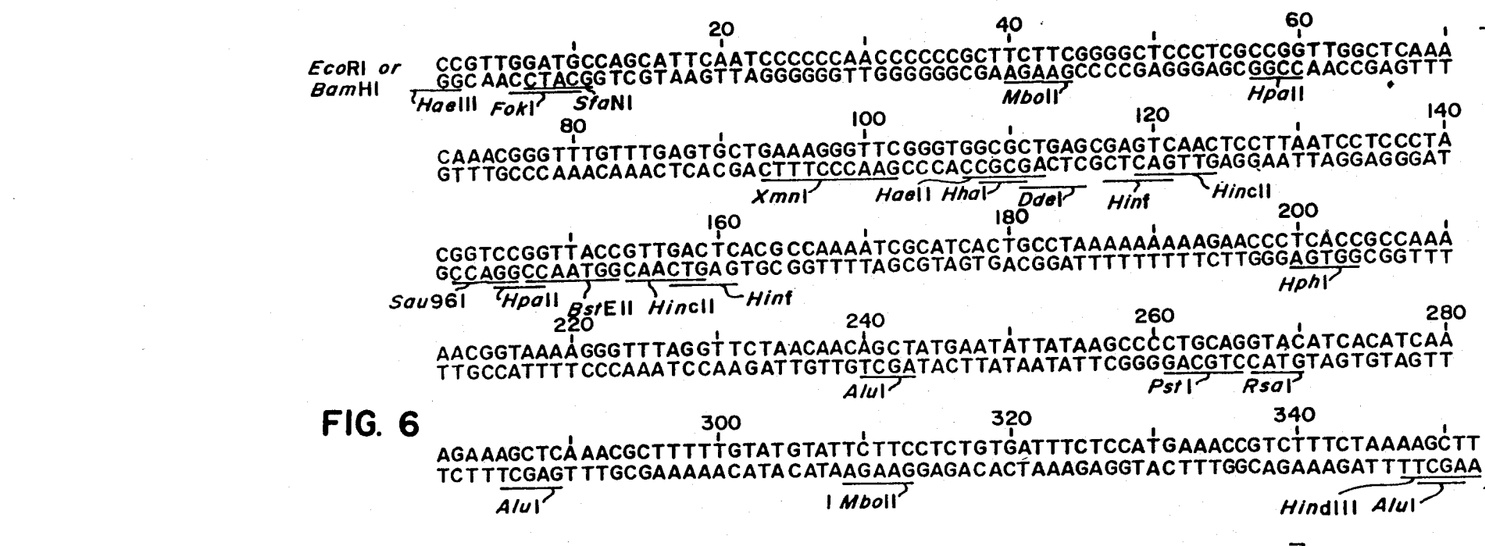
FIG. 6 shows the nucleotide sequence of a HaeIII to HindIII DNA fragment of approximately 350 base pairs contained within the 1.2 kb MboI Gram-positive partition fragment.
Figure 7:
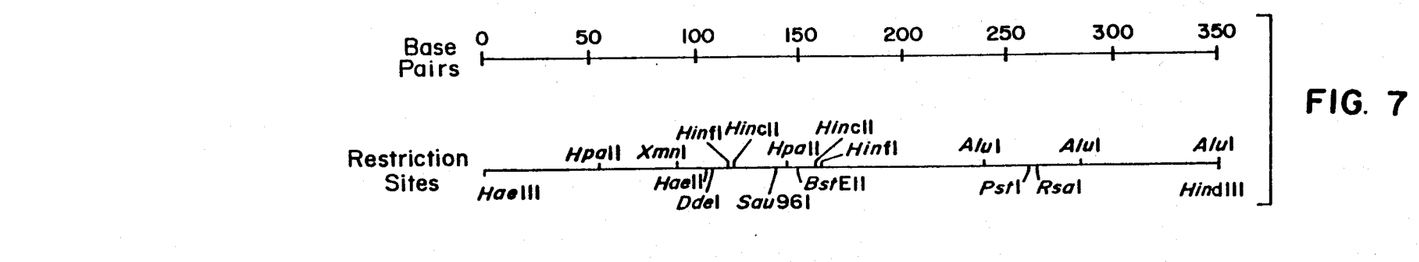
FIG. 7 shows a restriction enzyme map of a HaeIII to HindIII fragment of approximately 350 base pairs contained within the 1.2 kb MboI Gram-positive partition fragment.

The nucleotide sequence in the fragment of approximately 350 base pairs located between the HindIII and HaeIII sites in the 1.2 kb MboI Gram-positive partition fragment was determined. The sequence of this fragment is shown in FIG. 6.

To determine whether the Gram-positive partition proficiency function is located between the HaeIII and PstI sites within the 1.2 kb MboI fragment, a fragment of approximately 260 base pairs was isolated by digesting plasmid pOG2381 with restriction enzymes HaeIII and PstI. The 260 base pair fragment was purified on an agarose gel. Plasmid pDH5060 was digested with restriction enzyme EcoRI; the 5' protruding ends were filled in by DNA polymerase I Klenow fragment as described by Maniatis, T., et al., supra. The preparation was further digested with PstI enzyme to generate 2 fragments. The purified HaeIII - PstI fragment of approximately 260 base pairs was added at equal molar ratio to the preparation described above. It was then ligated with the digested pDH5060 fragments. The ligated DNA was used to transform *Escherichia coli* strain CS412. A tetracycline-resistant ampicillin-sensitive transformant was characterized further. It carries a plasmid designated pSYC730 which has the 260 base pair Gram-positive par+ fragment cloned in place of the small EcoRI to PstI fragment on pDH5060. Plasmid pSYC730 was transformed into *Bacillus subtilis* strain BD224 and then tested for partition proficiency. The results of partition proficiency test revealed that after 20 generations of growth in broth without chloramphenicol, *Bacillus subtilis* strain BD224 carrying plasmid pDH5060 was unstable. The same strain BD224 carrying par+ plasmid pSYC730 was stable. Thus it is concluded that the Gram-positive par+ proficiency is located within the approximate 260 base pair region flanked by the HaeIII and PstI sites as shown in FIG. 6.

EXAMPLE 7

The DNA sequence of the Gram-positive par+ proficiency function.

The sequence of the DNA from pSYC706 that contains the partition function was determined using the methods developed by Gilbert, W., and Maxam, A., in *Methods in Enzymology* 65:499-560 (edited by Grossman, L., and Moldave, K. J.) Academic Press, (1980). FIG. 6 shows the nucleotide sequence of this DNA. There is some ambiguity in the region around positions 60 to 70 due to compression which is probably caused by the presence of the GC - rich region adjacent to it (located between positions 20 to 65). However, many restriction enzyme sites found in this fragment, as predicted by sequence analysis, are also found by actual restriction enzyme digestion.

EXAMPLE 8

The Gram-positive par+ recombinant plasmids of the present invention show improved stability in Gram-positive recE+ transformed hosts.

It has been shown in the previous examples that the Gram-positive par+ recombinant plasmids of the present invention show improved stability when transformed into a recE− strain of *Bacillus subtilis* (BD224). As used herein, improved stability means that the recombinant plasmids with the Gram-positive par+ fragment are more stable than are identical plasmids that do not contain the Gram-positive par+ fragment. To determine whether the par+ plasmids show improved stability in a recE+ strain of *Bacillus subtilis*, the Gram-positive par+ recombinant plasmids were used to transform a recE+ strain of *Bacillus subtilis* (BD170 ). Except for being recE+, *Bacillus subtilis* strain BD170 is identical to strain BD224.

When *Bacillus subtilis* strain BD170 was transformed with plasmid pOG2381, it was 99% stable, i.e., pOG2381 was present in 99% of the transformed host cells, after 15 generations. When strain BD170 was transformed with pOG2428, it was 100% stable after 14 generations. Transformation techiniques were identical to those described in the previous examples.

EXAMPLE 9

The Gram-positive par+ fragment of the present invention shows an orientation dependency.

The partition fragment of the present invention can be inserted into the recombinant plasmids in two possible orientations. Only one orientation will show the partition phenotype. The reason for the orientation dependency of the par+ fragment is unclear.

It may be seen therefore that the invention provides compositions and methods useful for the production of engineered recombinant plasmids that include a partition segment which enhances the stability of the plasmids in Gram-positive host cell populations, especially growing Gram-positive host cell populations. The invention also provides par+ fragments as well as par+ engineered recombinant plasmids, i.e., engineered recombinant plasmids which include a Gram-positive partition segment. It further provides, engineered Gram-positive par+ recombinant plasmids which are substantially more partition stable than are identical plasmids that do not contin such a par+ partition fragment. Further, it provides Gram-positive organisms transformed with engineered par+ recombinant plasmids. The engineered par+ recombinant plasmids, and organisms transformed with them, are especially useful in industrial applications where long term growth or fermentation, e.g. a continuous fermentation process, is desired for the production of protein products.

Various modifications of the invention in addition to those shown and described herein will become apparent to those skilled in the art from the foregoing description. Such modifications are intended to fall within the scope of the appended claims.

REFERENCES

1. Gilbert, W., and Maxam, A., in *Method in Enzymology* 65:499–560 (edited by Grossman, L., and Moldave, K. J.) Academic Press, (1980).
2. Gray, O. and Chang, S., *J. Bacteriol.* 145:422–428 (1981).
3. Maniatis, T., Fritsch, E. F., and Sambrook, J., *Molecular Cloning: A Laboratory Manual,* Cold Spring Harbor Laboratory (1982).
4. McLaughlin, J., Chang, S. Y., and Chang, S., *Nucleic Acid Res.* 10:3905–3919 (1982).
5. Meacock, P. and Cohen, S., *Cell* 20:529–542 (1980).
6. Neugebauer, K., Sprengel, R., and Schaller, H., *Nucleic Acids Research* 9:2577–2588 (1981).
7. O'Callaghan, C., Morris, A., Kirby, S. M., and Shingler, A. H., *Antimicrob. Agents Chemother* 1:283–288 (1972).
8. Pritchard, R. H., Barth, P. T. and Collins J., *Symp. Soc. Gen. Microbiol.* 19:263–297 (1968).
9. Sutcliffe, J. G., *Nucleic Acids Res.* 5:2721–2728 (1978) and *Cold Spring Harbor Symp. Quant. Biol.* 43:77–90 (1979).
10. Tanaka, T., Kuroda, M., and Sakaguchi, K., *J. Bacteriol.* 129:1487–1494 (1977).

What is claimed is:

1. A method for creating engineered recombinant plasmids that will be partition proficient during Gram-positive host cell divisions comprising ligating a DNA fragment comprising a Gram-positive partition segment carried on at least one HaeIII - PstI fragment of approximately 260 base pairs isolated from the engineered recombinant *Bacillus Subtilis* plasmid pOG2381 (ATCC 39038) or the progeny thereof whereby said recombinant plasmids become partition proficient in a Gram-positive bacterial host.

2. The method according to claim 1 wherein said DNA fragment comprises a Gram-positive partition segment carried on at least one HindIII - HaeIII fragment of approximately 350 base pairs isolated from the engineered recombinant *Bacillus subtilis* plasmid pOG2381 (ATCC 39038) or the progeny thereof which are partition proficient in a Gram-positive bacterial host.

3. The method according to claim 1 wherein said DNA fragment comprises a Gram-positive partition segment carried on at least one MboI or Sau3A fragment of approximately 1.2 kb derived from the engineered recombinant *Bacillus subtilis* plasmid pOG2381 (ATTCC 39038) or the progeny thereof which are partition proficient in a Gram-positive bacterial host.

4. DNA fragments comprising Gram-positive partition segments carried on HindIII - HaeIII fragments of approximately 350 base pairs isolated from engineered recombinant plasmid pOG2381 (ATCC 39038) or the progeny thereof which are partition proficient in a Gram-positive bacterial host.

5. DNA fragments comprising Gram-positive partition segments carried on HaeIII - PstI fragments of approximately 260 base pairs isolated from engineered recombinant plasmid pOG2381 (ATCC 39038) or the progeny thereof which are partition proficient in a Gram-positive bacterial host.

6. A method for increasing, in a population of Gram-positive organisms harboring engineered recombinant plasmids which carry a selectable marker, the fraction of said organisms which are designated *Bacillus subtilis* strain BD224 (ATCC 39038) harboring a partition proficient plasmid, which comprises growing said organisms in the absence of the selection pressure corresponding to said selectable marker.

7. Transformable and compatible Gram-positive organisms wherein said organisms are *Bacillus subtilis* strain BD244 transformed by the partition proficient engineered recombinant plasmid pOG2381 (ATCC 39038) and the progeny thereof which are partition proficient.

8. Gram-positive partition proficient engineered recombinant plasmid pOG2381 (ATCC 39038) and the progeny thereof which are partition proficient.

* * * * *